United States Patent
Brown et al.

(10) Patent No.: US 9,535,049 B2
(45) Date of Patent: Jan. 3, 2017

(54) SAMPLE COLLECTING DEVICE FOR DROPLET AND GAS SAMPLING IN NARROW DUCTS OF A GAS TURBINE OR ANY OTHER DEVICE WITH AN OIL BREATHER

(71) Applicant: Siemens Aktiengesellschaft, Munich (DE)

(72) Inventors: Roger Brown, Middlesex (GB); Robert Pearce, Wickenby (GB)

(73) Assignee: Siemens Aktiengesellschaft, Munich (DE)

( * ) Notice: Subject to any disclaimer, the term of this patent is extended or adjusted under 35 U.S.C. 154(b) by 222 days.

(21) Appl. No.: 14/387,820

(22) PCT Filed: Feb. 13, 2013

(86) PCT No.: PCT/EP2013/052811
§ 371 (c)(1),
(2) Date: Sep. 24, 2014

(87) PCT Pub. No.: WO2013/143756
PCT Pub. Date: Oct. 3, 2013

(65) Prior Publication Data
US 2015/0041653 A1 Feb. 12, 2015

(30) Foreign Application Priority Data
Mar. 27, 2012 (EP) ..................... 12161508

(51) Int. Cl.
*G01N 1/20* (2006.01)
*G01N 33/28* (2006.01)
(Continued)

(52) U.S. Cl.
CPC ......... *G01N 33/2888* (2013.01); *F01D 21/003* (2013.01); *F01M 11/10* (2013.01);
(Continued)

(58) Field of Classification Search
CPC .. G01N 1/2035; G01N 1/2205; G01N 1/2247; G01N 2001/225; G01N 2001/2267; G01N 33/2888; F01M 13/00; B64D 33/04
See application file for complete search history.

(56) References Cited

U.S. PATENT DOCUMENTS

| 4,045,671 A | 8/1977 | Dille et al. |
| 4,164,653 A | 8/1979 | Matumoto et al. |

(Continued)

FOREIGN PATENT DOCUMENTS

| CN | 102052075 A | 5/2011 |
| DE | 10206026002 A1 | 12/2007 |

(Continued)

*Primary Examiner* — Blake A Tankersley
(74) *Attorney, Agent, or Firm* — Beusse Wolter Sanks & Maire

(57) ABSTRACT

An analyzing arrangement for analyzing a composition of a fluid, such as oil mist of an engine, e.g. a gas turbine is provided. The analyzing arrangement includes a breather pipe coupleable to the gas turbine such that at least a part of the fluid is flowing through the breather pipe, a first collecting device for collecting a first sample of the fluid, wherein the first collecting device is configured for providing a first composition analysis of the first sample and a second collecting device for collecting a second sample of the fluid, wherein the second collecting device is configured for providing a second composition analysis of the second sample. The first collecting device and the second collecting device are arranged inside the breather pipe such that the first collecting device and the second collecting device are exposed to a common flow characteristic of the fluid inside the breather pipe.

19 Claims, 2 Drawing Sheets

(51) Int. Cl.
  *G01N 1/22* (2006.01)
  *F01M 11/10* (2006.01)
  *F01D 21/00* (2006.01)
  *G01F 1/46* (2006.01)
  *G01J 3/28* (2006.01)
  *G01N 27/62* (2006.01)
  *F01M 13/00* (2006.01)

(52) U.S. Cl.
  CPC .................. *G01F 1/46* (2013.01); *G01J 3/28* (2013.01); *G01N 1/2035* (2013.01); *G01N 1/2205* (2013.01); *F01M 13/00* (2013.01); *F16N 2250/50* (2013.01); *G01N 27/626* (2013.01)

(56) References Cited

U.S. PATENT DOCUMENTS

| | | |
|---|---|---|
| 4,213,044 A | 7/1980 | Perrotta |
| 4,624,133 A | 11/1986 | Iwashita |
| 5,301,536 A | 4/1994 | Ortega et al. |
| 5,750,999 A | 5/1998 | Fox |
| H1757 H * | 11/1998 | Seltzer .................. G01N 1/2258 73/863 |
| 5,974,860 A | 11/1999 | Kuroda et al. |
| 6,369,890 B1 | 4/2002 | Harley |
| 7,748,280 B2 | 7/2010 | Jaffe et al. |
| 8,256,307 B2 * | 9/2012 | Graze, Jr. ............ G01N 1/2252 73/23.31 |
| 2002/0166365 A1* | 11/2002 | Kogure ................ G01N 1/2258 73/28.01 |
| 2002/0178729 A1 | 12/2002 | Care et al. |
| 2005/0087027 A1 | 4/2005 | Widmer |
| 2005/0160838 A1* | 7/2005 | Weaver ................ G01N 1/2247 73/863.03 |
| 2006/0242933 A1 | 11/2006 | Webb et al. |
| 2007/0039373 A1 | 2/2007 | Hoflinger et al. |
| 2008/0156073 A1 | 7/2008 | Borjon |
| 2009/0211370 A1* | 8/2009 | Ferri .................... G01N 1/2205 73/861.61 |
| 2010/0145634 A1 | 6/2010 | Pinguet et al. |
| 2015/0041653 A1 | 2/2015 | Brown et al. |

FOREIGN PATENT DOCUMENTS

| | | |
|---|---|---|
| DE | 102006026002 A | 12/2007 |
| EP | 1528385 A1 | 5/2005 |
| EP | 1757927 A2 | 2/2007 |
| EP | 1936358 A1 | 6/2008 |
| EP | 2831558 A1 | 2/2015 |
| GB | 2269675 A | 2/1994 |
| GB | 2350195 A | 11/2000 |
| GB | 2408798 A | 6/2005 |
| GB | 2398382 B | 2/2006 |
| GB | 2432425 A | 5/2007 |
| GB | 2447908 A | 10/2008 |
| JP | 2004219131 A | 8/2004 |
| JP | 2005164408 A | 6/2005 |
| JP | 2008157648 A | 7/2008 |
| RU | 2446389 C2 | 3/2012 |
| SU | 239910 A1 | 3/1969 |
| WO | 2013143756 A1 | 10/2013 |

\* cited by examiner

SAMPLE COLLECTING DEVICE FOR DROPLET AND GAS SAMPLING IN NARROW DUCTS OF A GAS TURBINE OR ANY OTHER DEVICE WITH AN OIL BREATHER

CROSS REFERENCE TO RELATED APPLICATIONS

This application is the US National Stage of International Application No. PCT/EP2013/052811 filed Feb. 13, 2013, and claims the benefit thereof. The International Application claims the benefit of European Application No. EP 12161508 filed Mar. 27, 2012. All of the applications are incorporated by reference herein in their entirety.

FIELD OF INVENTION

The present invention relates to an analysing arrangement for analysing a composition of a fluid of a gas turbine and to a method for analysing a composition of a fluid of a gas turbine by the analysing arrangement.

ART BACKGROUND

In the technical field of gas turbines there is a commercial requirement to measure the emissions from gas turbine engines in order to comply with national and regional environmental standards. In particular, there is a need to measure lube oil breather emissions from a gas turbine. The lube oil breather emission flows through a breather pipe in a liquid (droplet) and/or a gaseous aggregate state. The lube oil breather pipe comprises a relatively small diameter and the flow of the lube oil (mist) is relatively low and comprises high temperatures.

It is necessary to conduct simultaneous measurements of the liquid lube oil emissions and the gaseous lube oil emissions. However, often it is not possible from one single collecting device to receive a split sample (liquid/gas split) which provides sufficient amount of the measurement sample in the liquid state and/or the gas state for receiving a proper measurement result. Hence, in order to receive a proper measurement result, two measurement samples have to be taken from the fluid inside breather pipe, wherein in one test sample the liquid phase and in the other test sample the gaseous phase of the lube oil emission is analyzed.

In particular, the hydrocarbon amount of the lube oil emission in the gaseous phase and in the liquid phase is measured, so that a total amount of hydrocarbon of the lube oil breather emissions is analysed.

GB 2 408 798 A discloses a light scattering oil mist detecting device with means for preventing oil droplets entering the casing. The oil mist detecting device comprises a casing having an oil mist introducing chamber arranged in a crank-case of an internal combustion engine. A light emitting means and a photo detecting means of the oil mist detecting device may measure the oil mist introduced into the introducing chamber.

GB 2 398 382 A discloses an oil mist sampling device. The oil mist sampling device comprises light emitting means for radiating light and photo receiving means for receiving the radiated light. The photo receiving means outputs a signal corresponding to the intensity of the received light.

U.S. Pat. No. 6,369,890 B1 discloses a particle separation and detection apparatus. The apparatus comprises an analysing chamber which receives a gaseous fluid by diffusion from a receiving chamber connected via an inlet to an area being monitored. The gaseous fluid is measured by a photodiode which detects light scattered by particles in the gaseous fluid.

EP 1 936 358 A1 discloses an oil mist detector. A light emitting device irradiates light to a detection region in which oil mist is injected. The light is radiated through a transparent window. The received light is received through the transparent window by a receiving device.

SUMMARY OF THE INVENTION

It may be an object of the present invention to provide a proper analysis of lube oil breather emissions from a gas turbine.

This object may be solved by an analysing arrangement and by a method for analysing a composition of a fluid of a gas turbine by the analysing arrangement according to the independent claims.

According to a first aspect of the present invention, an analysing arrangement for analysing a composition of a fluid, in particular oil mist, of a gas turbine or any other device with an oil breather is described. The analysing arrangement comprises a first collecting device and a second collecting device which may be attached to a spool piece. The spool piece and hence the first collecting device and the second collecting device are placed in the oil breather pipe of the gas turbine. At least a part or a total amount of the fluid is flowing through the breather pipe. The first collecting device is adapted for collecting a first sample of the fluid. The analysing arrangement comprises further a second collecting device for collecting a second sample of the fluid. The first collecting device and the second collecting device are arranged inside the breather pipe such that the first collecting device and the second collecting device are exposed to a common flow characteristic of the fluid inside the breather pipe. The first collecting device is configured for providing a first composition analysis of the first sample and the second collecting device is configured for providing a second composition analysis of the second sample.

According to a further exemplary embodiment a method for analysing a composition of a fluid of the gas turbine or any other device with an oil breather by the above described analysing arrangement is presented. According to the method, a first sample of the fluid is collected by the first collecting device. Furthermore, according to the method, a second sample of the fluid is collected by the second collecting device.

The breather pipe is connected for example to a bearing housing of a gas turbine which provides a bearing of the shaft of the gas turbine or any other device (e.g. combustion engines) with an oil breather. Bearings of the gas turbine are lubricated generally with lube oil, for example. Due to high temperatures during operation of a gas turbine, oil mist may be generated. The oil mist comprises the oil in a first fraction, i.e. in a gaseous aggregate state, and in a second fraction, i.e. in a liquid aggregate state. The oil mist flows through the breather pipe e.g. to a collecting tank. The breather pipe may comprise a circular, elliptical or rectangular cross-sectional cross section.

There is a need to measure the composition of the fluid, i.e. the oil mist, which is exhausted through the breather pipe. In particular, there is a need to analyse the composition of the oil mist due to environmental requirements. Furthermore, the composition of the oil mist may provide information about certain defects of a gas turbine and defects of a bearing of the gas turbine, respectively.

Hence, the fluid (i.e. the respective first and second sample of the fluid) describes for example a mist of fluid, in particular an oil mist, which comprises a first fraction of oil which has a first aggregate state and a second fraction of the oil which has a second aggregate state. In particular, according to an exemplary embodiment, the first aggregate state of the first fraction of the fluid is a liquid aggregate state and the second aggregate state of the second fraction of the fluid is a gaseous aggregate state.

The first collecting device and the second collecting device may collect and optionally analyse the first and/or the second composition of the collected first and/or second sample of the fluid. For example, a respective collecting device (first collecting device or second collecting device) may collect and separate the respective sample of the fluid. The respective collecting device may forward the collected sample and specifically a liquid or gaseous fraction of the sample to a further analysing unit which may be located outside of the breather pipe. Alternatively the respective collecting device may analyse the composition, e.g. the amount of hydrocarbons, of the first (e.g. liquid) or the second (e.g. gaseous) fraction of the respective sample itself, i.e. internally. Specifically, each of the first collecting device and the second collecting device may comprise a respective opening section through which the respective first sample and the second sample may flow inside the respective first collecting device and the second collecting device.

By embodiments of the present invention, the respective first sample and the second sample which flow inside the respective first collecting device and the second collecting device have common flow characteristics, e.g. a common velocity. In particular, the opening section of the first collecting device and the opening section of the second collecting device may have a common distance to the pipe wall of the breather pipe. The distance may be defined as the shortest distance of a respective collecting device to the narrowest pipe wall.

Alternatively, in order to assure that the first collecting device and the second collecting device are exposed to a common flow characteristic (e.g. the velocity) of the fluid inside the breather pipe, the first collecting device and the second collecting device are spaced from the centre axis of the breather pipe with a common distance. The centre axis may define e.g. a symmetry line of the breather pipe. Moreover, the centre axis extends along a length extension of the breather pipe.

The first collecting device and/or the second collecting device may comprise an aerodynamic profile. In particular, the first collecting device and/or the second collecting device may comprise a housing with a wedge shape (i.e. in the region of the opening section), wherein a tip of the wedge-shaped collecting device is a leading edge against which the fluid inside the breather pipe flows. In particular, the respective opening section is formed in the tip of the wedge-shaped collecting device. Hence, such a trailing design of a collecting device minimizes the blockage and the back pressure of the fluid inside the breather pipe.

Furthermore, the first collecting device and/or the second collecting device may comprise a suction unit or may be connected to a suction unit, such that the first and/or second sample may be sucked into the respective inner volume of the first and/or second collecting device with a predefined velocity in order to generate an isokinetic flow of the fluid when entering the opening section.

In an exemplary embodiment, the first collecting device collects and separates the (e.g. liquid) first fraction of the first sample, such as the droplets in the first (oil mist) sample, from the (e.g. gaseous) second fraction of the first sample. The first collecting device may analyse the amount of hydrocarbon in the liquid oil fraction or may collect the (liquid) first fraction. After a predetermined time of collecting the (liquid) first fraction, the first collecting device and hence the collected (liquid) first fraction may be taken out of the breather pipe and analysed in an external laboratory, for example.

The second collecting device may separate the (e.g. liquid) first fraction from the (e.g. gaseous) second fraction of the second sample. The second collecting device may analyse the (e.g. gaseous) second fraction continuously. Additionally or alternatively a connection line may guide the (e.g. gaseous) second fraction to the external laboratory.

In order to analyse the respective first and second fraction of the fluid, the first collecting device and the second collecting device collect separately respective samples of the fluid from the fluid flow inside the breather pipe. This may be necessary, because from one common fluid collecting device it is complex to measure a highly correct hydrocarbon amount in each aggregates state of a sample, i.e. in a gaseous state and in a liquid state. Hence, two separate samples have to be taken from the fluid in the breather pipe, one by the first collecting device and another by the second collecting device.

In particular, if the liquid aggregate state of a sample fraction is measured, it has to be ensured that the sample flows in an isokinetic manner into the respective collecting device in order to collect an undistorted fluid sample, which means that the true amount of droplets and hence the amount of liquid fraction of the sample is collected by the respective collecting device. In order to achieve an isokinetic sample collection, the sample which is sucked into the collecting device has to have the same velocity as the fluid flowing through the breather pipe. Otherwise, an over-isokinetic or an under-isokinetic fluid flow is generated such that too much or too less droplets of the oil mist enter the respective collecting device and hence falsify the measurement. Hence, an entrance section or an opening section of each collecting device and a suction velocity of the sample through the collecting device has to be adapted to the velocity of the fluid through the breather pipe.

For these reasons, by embodiments of the present invention the fluid velocity of the fluid in the breather pipe enters the first collecting device and the second collecting device with a common velocity. This is achieved by arranging the first collecting device and the second collecting device inside the breather tube with a common distance from a pipe wall of the breather pipe or with a common distance from the centre axis of the breather pipe.

Generally, the fluid flowing through the breather pipe is decelerated by the friction between the fluid and the pipe wall. This causes some turbulence close to the pipe wall. Generally, in the centre of the breather pipe, the pipe flow and in particular the flow velocity of the fluid has a velocity maximum and close to the pipe wall, the pipe flow of the fluid has a velocity minimum. The velocity of the fluid in-side the breather pipe is equal within a radius or circle around the centre axis of the breather pipe.

Hence, by collecting the first and second samples by the two collecting devices, a check of sample integrity may be provided. For example, the first collecting device provides a first measurement of the droplet fraction and the second collecting device provides a second measurement of the droplet fraction. If the two droplet fraction measurements are within acceptable agreement, then this gives confidence that the gas analysis sample from the first and/or second collecting device is valid.

Hence, according to an exemplary embodiment, the first collecting device and the second collecting device comprise the common distance to the pipe wall because both collecting devices are arranged on a imaginary circle around the centre axis such that the fluid flowing against the first collecting device and the fluid flowing against the second collecting device have a common flow characteristic, such a common flow velocity. Furthermore, also further collecting device may be arranged on the imaginary circle within the breather pipe. Hence, by embodiments of the present invention a proper and exact collection of a first sample and a second sample for the respective first collecting device and second collecting device is achieved.

According to a further exemplary embodiment, the breather pipe has a centre axis. The first collecting device and the second collecting device are arranged inside the breather pipe one after another with an offset between each other along the centre axis. The offset may be defined between a downstream end of the first collecting device along the centre axis and the beginning, i.e. the upstream located opening section, of the second collecting device to minimize disturbance of the fluid at the second collecting device or vice versa. Hence, if the first collecting device and the second collecting device are arranged one after another along the centre axis, the flow of the fluid inside the breather pipe is less distorted such that a more undistorted first sample and second sample may be collected.

According to a further exemplary embodiment, the first collecting device comprises a first separator unit for separating a first fraction with a first aggregate state of the first sample from a second fraction with a second aggregate state of the first sample.

Additionally or alternatively, the second collecting device comprises a second separator unit for separating a further first fraction with the first aggregate state of the second sample from a further second fraction with a second aggregate state of the second sample.

The respective first and second separator unit may comprise for example a filter. The filter may comprise for example quartz wool and/or a filter membrane in order to separate the first fraction and the second fraction from the respective sample.

According to a further exemplary embodiment, the first collecting device and/or the second collecting device comprises a temperature sensor, such as a thermometer, for measuring a temperature of the fluid and the first or second sample, respectively.

According to a further exemplary embodiment, the first collecting device and/or the second collecting device comprise a pressure gauge, in particular a pitot gauge, for measuring a pressure of the fluid.

Hence, by measuring the temperature with the thermometer and the pressure by the pressure gauge, the flow characteristics of the fluid inside the breather pipe may be determined. Hence, by knowing the temperature and the pressure of the fluid, an isokinetic flow of the fluid at the opening section of the first collecting device or the second collecting device through a respective opening may be adjusted more efficiently. Furthermore, the pressure and the temperature of the fluid may give hints to a failure operation of the bearing of the gas turbine or the gas turbine itself.

According to a further exemplary embodiment, the first collecting device comprises a first analysing unit for analysing the first sample in the first collecting device. The first analysing unit may be an optical analysing device.

Additionally or alternatively, the second collecting device comprises a second analysing unit for analysing the second sample in the second collecting device. The second analysing unit may be also an optical analysing device.

Hence, according to an exemplary embodiment of the method, the first sample is analysed within the first collecting device and/or the second sample is analysed within the second collecting device.

After separation of the first fraction and the second fraction of the respective samples, the first collecting device and/or the second collecting device may comprise the above described analysing units which are adapted for applying analyzing methods in order to measure the composition of the first fraction and/or the second fraction of the respective sample. For example, chemical analyzing methods and/or optical analyzing methods may be applied in order to measure a desired composition of the respective fraction. For example, the composition to be analysed may be for example the amount of methane only hydrocarbon (MOHC), of carbon monoxide (CO), of carbon dioxide (CO2) and of total hydrocarbons (THC).

In particular, the respective first and/or second optical measurement device may be an infrared spectrophotometer. By such an infrared spectrophotometer in particular the fraction of the respective sample in the liquid aggregate state may be measured. The liquid fraction of the collected sample in a collecting device may be separated by the separator from the gaseous fraction of the fluid.

The separating unit may collect the liquid fraction of the fluid by a quartz or glass wool. The liquid fluid may be extracted from the glass wool by solvents, for example. The measurement of the liquid fraction of the fluids by infrared spectrophotometer may lead to an improved sensitivity and reproducibility.

The gaseous fraction of the respective sample may be measured by a flame ionization detector (FID). By the flame ionization detector in particular a volatile organic compounds (VOC), such as hydrocarbons, in a composition of the respective sample may be measured. A flame ionization detector is based on the measuring of the conductivity of a flame gaseous fluid between two electrodes, wherein hydrogen is used as a burnable gas and which is mixed together with the gas fraction of the fluid. In this process electrons are released which get caught by a surrounding metallic wire. This results in a changed conductivity so that the composition of the gas fraction may be determined.

Additionally or alternatively, the gathered liquid fraction of the sample may be weight by a weighting unit installed in a respective one of the first and/or second collecting device in order to measure the weight of extracted liquid fraction from the fluid.

According to a further exemplary embodiment, at least one of the first collecting devices and the second collecting devices comprises an inner volume and the opening section through which a respective sample of the fluid is entered into the inner volume.

According to a further exemplary embodiment, the opening section is detachably fixed to the respective first collecting device or the second collecting device.

Hence, the respective first sample and the second sample may enter the inner volume of the respective collecting device through the respective opening section. Inside the inner volume e.g. the separator unit and/or analysing units, such as the optical analysing device, may be installed.

Furthermore, a connection line may be coupled to the inner volume of the first collecting device or the second collecting device. The connection line may be further coupled to an external device in order to couple the inner volume with the externally arranged external device, such as the FID detector. Hence, a desired fraction of a respective sample may be drained off from the inner volume and may be guided through the connection line to the external device which is located in a laboratory, for example. Hence, by providing a connection line, in particular for the gaseous fraction of the sample, critical measurement methods, such as the FID analysis which uses a flame which may cause a burning of the gaseous fraction, may be conducted spaced apart from the breather pipe. Hence, safety requirements may be met and a safe measurement method is achieved.

In an exemplary embodiment, the at least one of the first collecting device and the second collecting device is connected by the connection line to the external device. Inside the respective inner volume, the respective separator unit separates the gaseous fraction from the liquid fraction of the respective sample. The gaseous fraction is guided through the connection line to the external analyzing device. The liquid fraction is gathered within the e.g. glass wool of the separator unit. After a predetermined time of collecting the sample inside the respective collecting device, the soaked glass wool may be taken out of the respective collecting device. In a laboratory, the liquid fraction is separated from the glass wool and the amount and the composition of the liquid fraction are analysed. Hence, the liquid droplet fraction may be measured offline (e.g. when the analysing arrangement is not inside the breather pipe) in a laboratory whilst the gas analysis may be performed continuously online (e.g. when the analysing arrangement is located inside the breather pipe and the engine, e.g. the gas turbine, is operating).

The connection line may comprise a length of approximately 5 m to approximately 25 m (meters), particularly 15 m to 20 m, such that the gaseous fraction may be analysed in a safe distance with respect to the breather pipe. Furthermore, the connecting line may be trace heated, e.g. a heating element, a heating braid or a heating jacket, in order to keep the temperature and hence the fluid flow characteristic of the gaseous fraction to be analysed approximately unchanged. Hence, unbiased analysing results even spaced apart from the breather pipe may be achieved.

According to an exemplary embodiment of the method, the velocity, the pressure and/or the temperature of the fluid flowing through the breather pipe is measured. Hence, the flow characteristics of the fluid inside the breather pipe may be determined such that for example an isokinetic sample collection is adjustable.

In particular, according to an exemplary embodiment of the method, a diameter of an opening section of at least one of the first collecting devices and the second collecting devices are adjusted depending on the measured velocity, the measured pressure and/or the measured temperature of the fluid flowing through the breather pipe such that the fluid flows in an isokinetic manner through the opening into an inner volume of the respective first collecting device or the respective second collecting device.

Hence, the analysing arrangement may be installed at different breather pipes e.g. from different gas turbines, wherein the analysing arrangement may be adjusted to the individual flow conditions of the fluid flowing through a respective breather pipe. By adjusting the diameter of the opening of the respective collecting device, the measurement adjustment may be adapted to different operating conditions so that an isokinetic flow through the opening is provided even at various operating conditions.

Hence, the analysing arrangement may be detachably mounted to a breather pipe, such that the analysing arrangement may be used for different breather pipes of e.g. different gas turbines.

By providing a common velocity of the fluid at the first collecting device for measuring a first aggregate state of the fluid and at the separated second collecting device which measures the second aggregate state of the fluid, it is ensured that a split between mass or volume ratios of the aggregate states (such as a liquid/gas split) within the first sample and the second sample is approximately constant.

Hence, a more reliable measurement result is achieved. By knowing the flow characteristics of the fluid inside the breather pipe and by selecting an appropriate opening of the opening section, an isokinetic flow inside the respective inner volume of the respective collecting device is achieved which improves the measurement of the samples, in particular of the liquid fraction of the sample.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims is considered as to be disclosed with this application.

BRIEF DESCRIPTION OF THE DRAWINGS

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
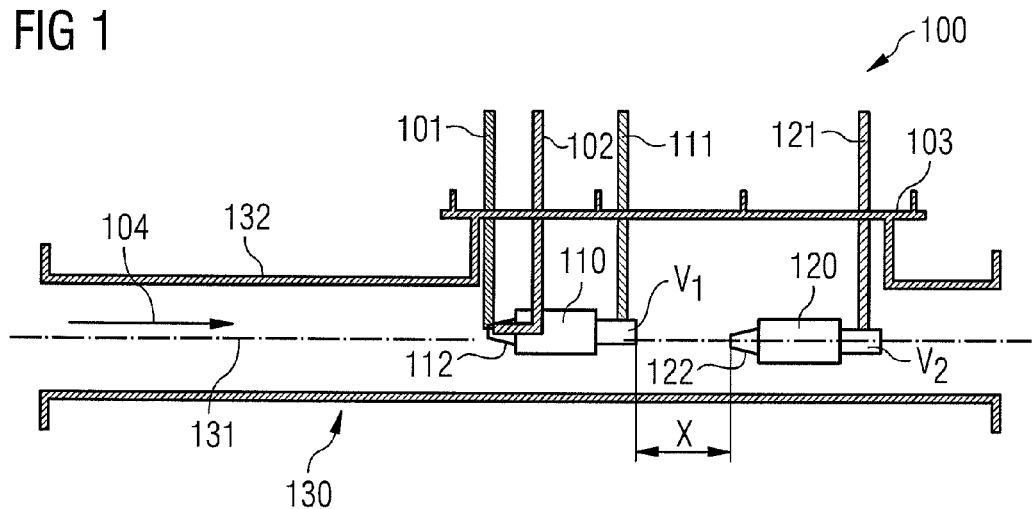
FIG. 1 shows a schematical view of an analysing arrangement according to an exemplary embodiment of the present invention.

The illustrations in the drawings are schematical. It is noted that in different figures, similar or identical elements are provided with the same reference signs.

FIG. 1 shows an analysing arrangement 100 for analysing a composition of a fluid of a gas turbine. The analysing arrangement 100 comprises a breather pipe 130, a first collecting device 110 and a second collecting device 120. The breather pipe 130 is coupleable to the gas turbine such that a part of the fluid, such as an oil mist from a bearing section of the gas turbine, is flowing through the breather pipe 130 with the flow direction 104. The first collecting device 110 collects the first sample of the fluid and optionally analyses the first sample. A second collecting device 120 collects a second sample of the fluid and optionally analyses the second sample.

The first collecting device 110 and the second collecting device 120 are arranged inside the breather pipe 130 such that the fluid has at the leading edge (upstream edge) of the first collecting device 110 and at the leading edge (upstream edge) of the second collecting device 120 the same flow characteristics. In order to provide common flow characteristics of the fluid at the first collecting device 110 and the second collecting device 120, the first collecting device 110 and the second collecting device 120 have a common distance d to a pipe wall 132 of the breather pipe 130. The distance d may be taken from the cross-sectional view in FIG. 2.

The breather pipe 130 comprises a centre axis 131 which may be for example the symmetry axis of the breather pipe 130. The centre axis 131 is surrounded by the pipe wall 132. The first collecting device 110 comprises a first opening section 112 through which the sample of the fluid flowing through the breather pipe 130 may enter the first collecting device 110. The first sample may flow further to an inner volume VI of the first collecting device 110. In the inner volume VI of the first collecting device 110 the first sample may be separated into a first fraction of a first aggregate state and into a second fraction of a second aggregate state.

The first aggregate state may be a gaseous aggregate state and the second aggregate state may be a liquid aggregate state of the first sample. The first fraction and the second fraction may be separated by a separation unit, which may comprise a filter 301, for example (see FIG. 3). From the inner volume VI of the first collecting device 110 a connection line 111 is coupled to an external device, such as a control device or a further analyzing device. The first connection line 111 may be for example a data line or a fluid line which guides the first and/or the second fraction of the first sample to e.g. an external analyzing unit.

Furthermore, inside the inner volume V1, an internal analyzing unit may be installed, such as an infrared spectrophotometer, for example.

As can be taken from the first collecting device 110, a thermometer 101 (e.g. a resistance thermometer or a thermocouple) and a pressure gauge 102 may be attached, such that the flow characteristics of the fluid and/or the first sample may be measured.

The opening section 112 of the first collecting device 110 comprises an opening with a predefined diameter such that the fluid is flowable into the inner volume V1. Furthermore, the opening section 112 may form a nozzle type section which may be detachably mounted to a body of the first collecting device 110. As can be taken from FIG. 1, the opening section 112 may comprise a wedge-shape in order to improve the aerodynamic profile of the first collecting device 110.

Furthermore, the second collecting device 120 may be arranged with a predefined axial offset x along the centre axis 131 with respect to the first collecting device 110. Hence, by providing a predefined offset x between both collecting de-vices 110, 120 the turbulences of the fluid which passes the first collecting device 110 may be reduced such that at a downstream located second opening section 122 of the second collecting device 120 an almost laminar and undisturbed flow of the fluids inside the breather pipe 130 is achieved again. Hence, the fluid characteristics and parameters at the first opening section 112 are identical to the flow parameters of the fluid at the second opening section 122. Hence, a more precise extraction and analysing of the first sample and the second sample are achieved.

Similarly to the first collecting device 110, the second collecting device 120 comprises a second inner volume V2. A second connection line 121 may connect the second collecting device 120 to an (further) external analyzing unit or a (further) control unit.

Furthermore, as can be taken from FIG. 1, the first collecting device 110 and the second collecting device 120 may be attached to a spool piece 103, wherein the spool piece 103 may be detachably arranged to e.g. a flange, of the breather pipe 130. Hence, the spool piece 103 together with the first collecting device 110 and the second collecting device 120 may be used for a plurality of different breather pipes 130. Hence, a flexible analysing arrangement 100 may be provided.

The spool piece 103 may have a length along the axial direction along the centre line 131 of approximately 350 mm to approximately 450 mm (millimeters). Each of the first collecting device 110 and the second collecting device 120 may have a length along the axial direction of approximately 110 mm to approximately 130 mm. The offset x between the trailing edge (downstream end) of the first collecting device 110 and the leading edge (upstream end) of the second collecting device 120 may be approximately 90 mm to approximately 110 mm. The breather pipe 130 may have a diameter of approximately 90 mm to approximately 110. Specifically, the offset x may have approximately the same value as the diameter of the breather pipe 130. The dimensions given above may vary depending on the size of the gas turbine.

Figure 2:
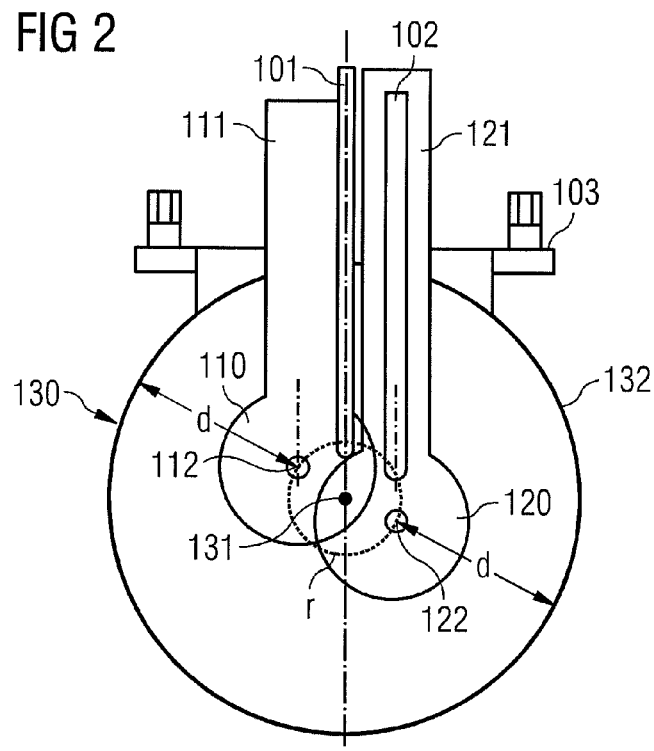
FIG. 2 shows a cross-sectional view of a breather pipe of the analysing arrangement according to an exemplary embodiment of the present invention.

FIG. 2 shows a cross-sectional view of the breather pipe 130 and the respective first collecting device 110 and second collecting device 120. In order to outline the arrangements of the respective first collecting device 110 and the second collecting device 120 a circle r is highlighted which comprises the same radius with respect to the centre axis 131. As can be taken from FIG. 2, the first collecting device 110 and the second collecting device 120 are arranged within the breather pipe 130 such that (e.g. the opening section 112 of) the first collecting device 110 and (e.g. the second opening section 122 of) the second collecting device 120 comprise a common distance d to the pipe wall 132 of the breather pipe 130. Hence, the fluid which streams against the first collecting device 110 and the second collecting device 120 comprises the same velocity. Hence, more precise first and second samples may be taken which have equal flow characteristics. Hence, more efficient measurement results may be achieved.

Specifically, the first collecting device 110 and the second collecting device 120 are arranged within the breather pipe 130 such that (e.g. the opening section 112 of) the first collecting device 110 and (e.g. the second opening section 122 of) the second collecting device 120 are spaced from the centre axis 131 with a common distance. Furthermore, (e.g. the opening section 112 of) the first collecting device 110 and (e.g. the second opening section 122 of) the second collecting device 120 are spaced apart from each other along a radial direction, wherein both collecting devices 110, 120 may have the same common distance to the pipe wall 132 and/or the centre axis 131. Hence, the collecting devices 110, 120 are offset with respect to each other around the centre axis 131. The radial direction describes a direction which is perpendicular to the centre axis 131 and which intersects with the centre axis 131.

As shown in FIG. 2, the first collecting device 110 and the second collecting device 120 are arranged within the breather pipe 130 such that (e.g. the opening section 112 of) the first collecting device 110 and (e.g. the second opening section 122 of) the second collecting device 120 are located at different circumferential locations onto the circle r. Specifically, the (e.g. the opening section 112 of) the first collecting device 110 is located at a first location onto the circle r and (e.g. the second opening section 122 of) the second collecting device 120 is located at a second location onto the circle r, wherein the second location is spaced apart from the centre axis 131 along an opposite direction with respect to the first location.

In FIG. 2, a protection plane is shown at which the first collecting device 110 and the second collecting device 120 are protected along the centre axis 131 which functions as the protection direction. As shown in FIG. 2, the first collecting device 110 and the second collecting device 120 are spaced apart along the centre axis 131 and are spaced apart from each other within the protection plane. Hence a fluid flow along the centre axis 131 flowing at the second downstream located second collecting device 120 is not disturbed by the upstream located the first collecting device 110.

Furthermore, in FIG. 1 the thermometer 101 and the pressure gauge 102 are shown. Respective sensors of the thermometer 101 and the opening of a pitot tube of the pressure gauge 102 may measure the fluid which flows in a region of the circle r. Hence, the temperature and the pressure are measurable which comprise the same and comparable parameters of the fluid entering the respective collecting device 110, 120. The temperature sensor 101 used may be a thermometer e.g. a resistance thermometer, or for example may be a thermocouple.

Figure 3:
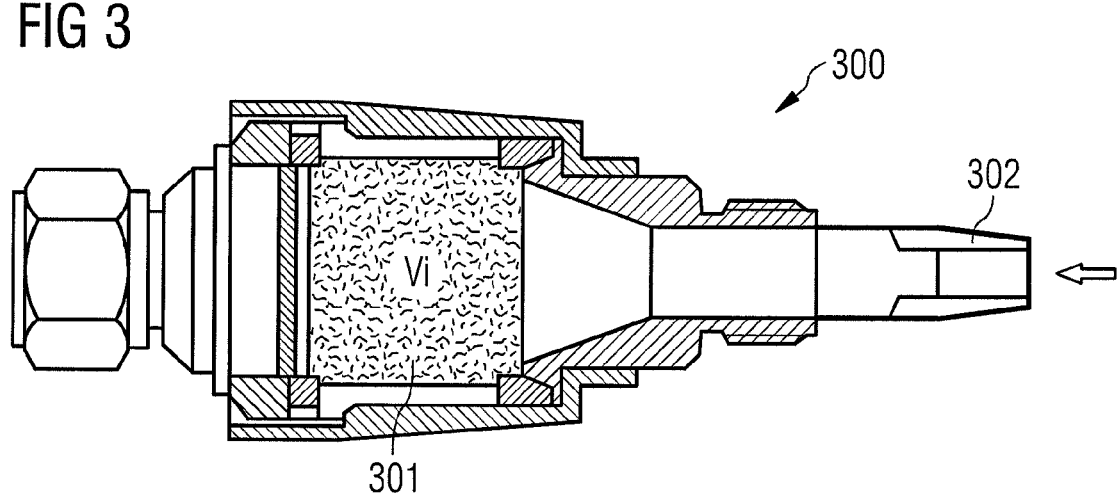
FIG. 3 shows a schematical view of a collecting device according to an exemplary embodiment of the present invention.

FIG. 3 shows an exemplary embodiment of a collecting device 300. The collecting device 300 may be installed in the breather pipe 130 for the first collecting device 110 or for the second collecting device 120. As can be taken from FIG. 3, the collecting device 300 comprises an opening section 302 which may be detachably mounted to the collecting device 300. The input flow direction is indicated by the arrow in FIG. 3. The collecting device 300 shows a filter 301 which is in-stalled inside the inner volume Vi of the collecting device 300. The filter 301 may be part of the separator unit. The filter 301 may be made of a quartz or glass wool such that the liquid part of the respective sample may be separated and gathered in the filter 301.

Figure 4:
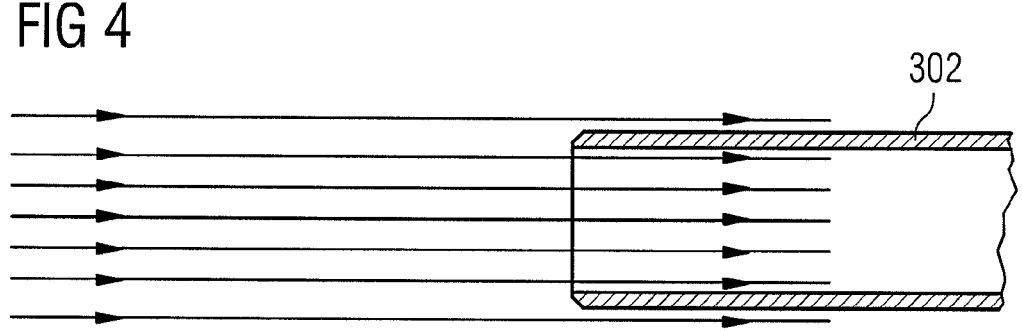
FIG. 4 shows a schematical view of an isokinetic flow of the fluid entering an opening section of a respective collecting device.

FIG. 4 shows a schematical view of an isokinetic stream of the fluid which enters the opening of the opening section 302. As can be taken from FIG. 4, the flow lines of the fluid are parallel also that the opening section 302 of the respective collecting device 300. Hence, a respective sample may be captured in an undistorted manner.

It should be noted that the term "comprising" does not exclude other elements or steps and "a" or "an" does not exclude a plurality. Also elements described in association with different embodiments may be combined. It should also be noted that reference signs in the claims should not be construed as limiting the scope of the claims.

The invention claimed is:

1. An analysing arrangement for analysing a composition of a fluid of a gas turbine, the analysing arrangement comprising:
a breather pipe configured to be coupled to the gas turbine such that at least a part of the fluid is flowing through the breather pipe,
a first collecting device for collecting a first sample of the fluid, wherein the first collecting device is configured for providing a first composition analysis of the first sample, and
a second collecting device for collecting a second sample of the fluid, wherein the second collecting device is configured for providing a second composition analysis of the second sample,
wherein the first collecting device and the second collecting device are arranged inside the breather pipe such that the first collecting device and the second collecting device are exposed to a common flow characteristic of the fluid inside the breather pipe; and
wherein the first collecting device and the second collecting device are offset with respect to each other around a centre axis of the breather pipe and have a common distance (d) to a pipe wall of the breather pipe.

2. The analysing arrangement according to claim 1, wherein the breather pipe has a centre axis, wherein the first collecting device and the second collecting device are arranged inside the breather pipe with an offset (x) between each other along the centre axis to minimize disturbance of the fluid.

3. The analysing arrangement according to claim 1, wherein the first collecting device comprises a first separator unit for separating a first fraction with a first aggregate state of the first sample from a second fraction with a second aggregate state of the first sample, and/or wherein the second collecting device comprises a second separator unit for separating a further first fraction with the first aggregate state of the second sample from a further second fraction with the second aggregate state of the second sample.

4. The analysing arrangement according to claim 1, wherein the first collecting device and/or the second collecting device comprise (s) a temperature sensor for measuring a temperature of the fluid.

5. The analysing arrangement according to claim 1, wherein the first collecting device and/or the second collecting device comprise(s) a pressure gauge, for measuring a pressure of the fluid.

6. The analysing arrangement of claim 5, wherein the pressure gauge is a pitot gauge.

7. The analysing arrangement according to claim 1, wherein the first collecting device comprises a first analysing unit for analysing the first sample in the first collecting device.

8. The analysing arrangement of claim 7, wherein the first analysing unit is an optical analysing device.

9. The analysing arrangement according to claim 1, wherein the second collecting device comprises a second analysing unit for analysing the second sample in the second collecting device.

10. The analysing arrangement of claim 9, wherein the second analysing unit is an optical analysing device.

11. The analysing arrangement according to claim 1, wherein at least one of the first collecting device and the second collecting device comprises an inner volume and an opening section through which a respective sample of the fluid is streamable into the inner volume.

12. The analysing arrangement according claim 11, wherein the opening section is detachably fixed to the respective first collecting device or the second collecting device.

13. A method for analysing a composition of a fluid of a gas turbine by an analysing arrangement according to claim 1, the method comprising:

collecting a first sample of the fluid by the first collecting device, and collecting a second sample of the fluid by the second collecting device.

14. The method according to claim 13, further comprising analysing the first sample within the first collecting device, and/or analysing the second sample within the second collecting device.

15. The method according to claim 13, further comprising measuring the velocity, the pressure and/or the temperature of the fluid flowing through the breather pipe.

16. The method according to claim 15, further comprising adjusting a diameter of an opening of an opening section of at least one of the first collecting device and the second collecting device dependent on the measured velocity, the pressure and/or the temperature of the fluid flowing through the breather pipe such that the fluid flows in an isokinetic manner through the opening into an inner volume of the respective first collecting device or the respective second collecting device.

17. The analysing arrangement of claim 1, wherein the composition of fluid is an oil mist.

18. An arrangement for analysing a composition of a fluid passing through a breather pipe of a gas turbine, the arrangement comprising:

a first collecting device comprising a first inlet positioned within the breather pipe for collecting a first sample of the fluid, wherein the first collecting device is configured for providing a first composition analysis of the first sample; and a second collecting device comprising a second inlet positioned within the breather pipe for collecting a second sample of the fluid, wherein the second collecting device is configured for providing a second composition analysis of the second sample;

wherein the first inlet and the second inlet each have an inlet centre axis circumferentially offset from each other along a circle having a radius (r) from a centre axis of the breather pipe such that the first sample and the second sample are obtained with equal flow characteristics.

19. The arrangement of claim 18, wherein the first inlet centre axis and the second inlet centre axis are disposed at locations diametrically opposite each other along the circle.

* * * * *